United States Patent [19]

Block et al.

[11] 4,019,056
[45] Apr. 19, 1977

[54] INFRARED LASER DETECTOR EMPLOYING A PRESSURE CONTROLLED DIFFERENTIAL OPTOACOUSTIC DETECTOR

[75] Inventors: Barry Block, Los Altos Hills; Harry E. Aine, Mountain View, both of Calif.

[73] Assignee: Diax Corporation, Sunnyvale, Calif.

[22] Filed: Apr. 28, 1975

[21] Appl. No.: 572,013

[52] U.S. Cl. .............................................. 250/344
[51] Int. Cl.² .......................................... G01J 3/42
[58] Field of Search .......... 250/343, 339, 344, 345, 250/350; 356/97

[56] References Cited

UNITED STATES PATENTS

| | | | |
|---|---|---|---|
| 3,005,097 | 10/1961 | Hummel | 250/343 |
| 3,105,147 | 9/1963 | Weilbach et al. | 250/344 |
| 3,727,050 | 4/1973 | Kerr | 250/343 |
| 3,793,525 | 2/1974 | Burch et al. | 250/343 |
| 3,820,901 | 6/1974 | Kreuzer | 356/97 |
| 3,893,771 | 7/1975 | Bell | 356/97 |

Primary Examiner—Alfred E. Smith
Assistant Examiner—B. C. Anderson
Attorney, Agent, or Firm—Lowhurst & Aine

[57] ABSTRACT

An infrared laser absorption spectrometer is disclosed wherein a pair of detector cells are disposed serially along the laser beam path. The laser beam is modulated to produce a modulation of the absorption by the sample materials in the two cells. Modulated absorption by the samples produces an acoustic wave in each cell which is detected by a suitable microphone and subtracted so as to produce a difference signal corresponding to the difference in infrared absorption between the two cells so that undesired background effects common to both cells are cancelled. A pressure controller, which is responsive to the pressure difference between the sample pressure in the two cells at a frequency substantially below the beam modulation frequency is employed for controlling the pressure differential. In one embodiment the pressure controller includes a compliant membrane partitioning the two cells so that the membrane may move so as to equalize the pressures. In a second embodiment, deflection of the diaphragm of a differential microphone coupled into both cells is employed to derive an output utilized to control either the flow through the cells and/or the volume of the respective cells to control the pressure difference between the cells.

19 Claims, 4 Drawing Figures

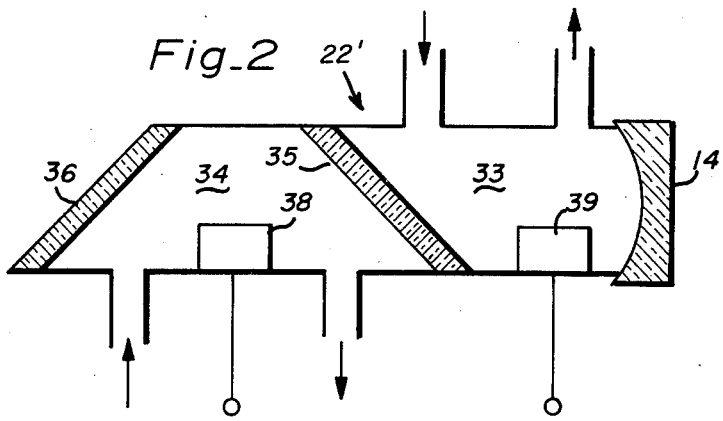
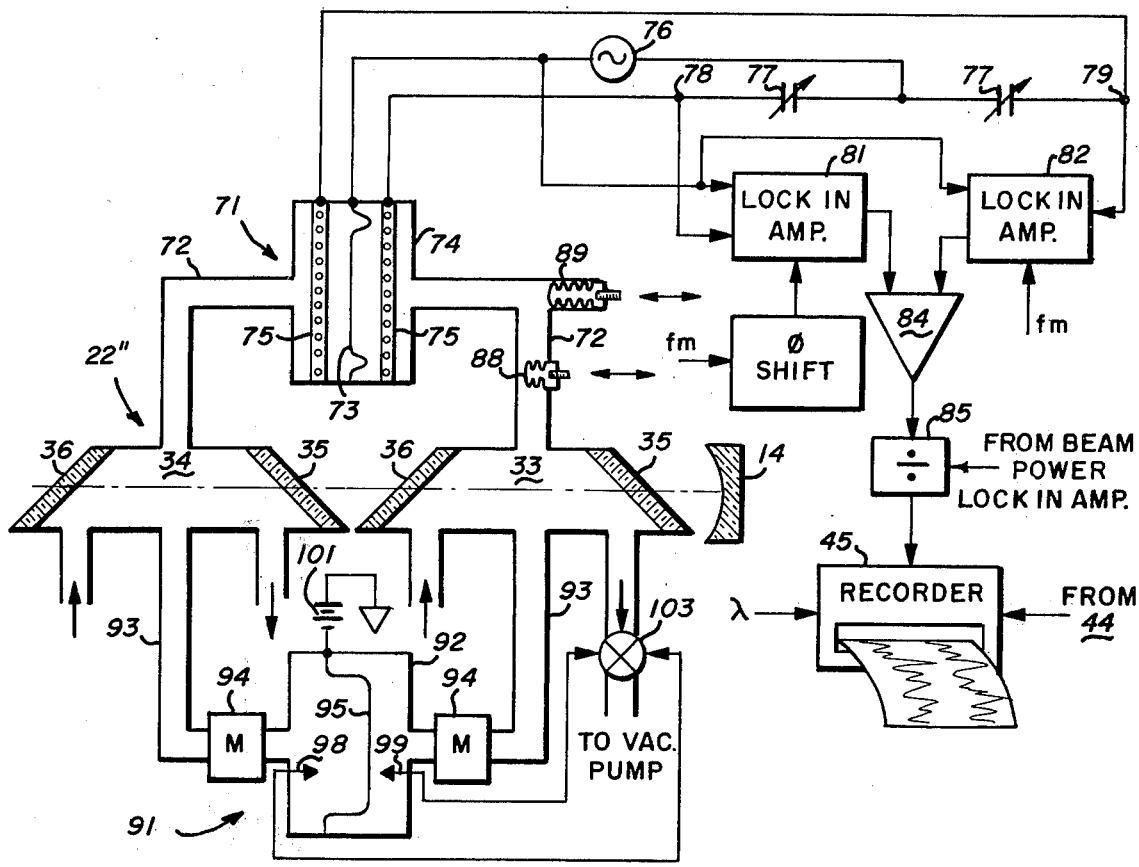

INFRARED LASER DETECTOR EMPLOYING A PRESSURE CONTROLLED DIFFERENTIAL OPTOACOUSTIC DETECTOR

RELATED CASES

An infrared laser spectrometer having dual optoacoustic detector cells serially arranged along the beam path is disclosed and claimed in copending U.S. application Ser. No. 565,008 filed Apr. 4, 1975.

BACKGROUND OF THE INVENTION

The present invention relates in general to laser infrared absorption spectroscopy and more particularly to such spectroscopy employing an optoacoustic detector for detecting absorption of energy by the sample from the laser beam.

DESCRIPTION OF THE PRIOR ART

Heretofore, infrared laser absorption spectroscopy has employed an optoacoustic sample detection cell for analyzing gaseous samples and, in particular, for detecting certain pollutants in the air to concentration levels as low as parts per billion. Such a laser spectrometer is disclosed in: U.S. Pat. No. 3,820,901 issued June 28, 1974; in an article titled "Laser Optoacoustic Spectroscopy: A New Technique of Gas Analysis" appearing in *Analytical Chemistry*, Vol. 46, No. 2 of February 1974, pages 239–244; in *Science*, Vol. 177, pages 347–349 of July 18, 1972 in an article titled "Air Pollution: Sensitive Detection of Ten Pollutant Gases by Carbon Monoxide and Carbon Dioxide Lasers"; and in U.S. Pat. No. 3,659,452 issued May 2, 1972.

In these prior art laser absorption spectrometers, the laser, which is preferably a relatively high power output carbon dioxide or carbon monoxide laser, produces an output laser beam which is turnable to selected wavelengths within a band of infrared wavelengths of interest, i.e., the band of wavelengths over which certain gaseous sample constituents of interest are known to have infrared absorption spectra. The laser output beam is directed through an optoacoustic cell containing the gaseous material to be analyzed. A sensitive microphone is coupled to the gaseous sample inside the sample cell. The laser beam is chopped at a certain chopping frequency, as of 25 Hertz, to produce a corresponding modulation of the absorption, of the laser beam energy by the sample gas under analysis. Absorption of energy from the laser beam by the gas produces heating thereof which results in generating an acoustic wave or quasi-static pressure field, at the chopping frequency, which is detected by the microphone. The detected signal is processed to produce an output signal as a function of the wavelength of the infrared energy of the tunable laser beam to derive an absorption spectrum of or absorption spectral data concerning the sample under analysis.

It is also known from the prior art to identify and resolve the retention time peaks of the effluent of a retention time chromatograph by feeding the effluent stream of the column through the optoacoustic detection cell of an infrared laser absorption spectrometer. Mufflers were provided for acoustically isolating the optoacoustic cell from the chromatographic column and from a flame ionization detector disposed downstream of the fluid passing through the optoacoustic cell. Such a combined IR laser absorption spectrometer and retention time chromatograph is disclosed in copending U.S. application Ser. No. 551,379, filed Feb. 20, 1975.

One of the problems encountered in an infrared laser absorption spectrometer is that undesired background signals are encountered. Some of these background signals are due to the heating of the windows of the optoacoustic cell. This problem is particularly pronounced when the modulation frequency of the laser beam is very low, i.e., on the order of one Hertz. In addition, the carrier gas which carries the sample material can have undesired absorption lines in the infrared spectrum which may produce interferring and spurious absorption lines in the spectrum of the material under analysis. Furthermore, if air is utilized as the carrier gas, contaminants in the air will appear as signals due to the absorption of the infrared radiation from the beam by the contaminants in the air. Also, many carrier gases are not sufficiently pure and their contaminants will introduce unwanted absorption lines superimposed on the spectrum of the sample under analysis.

It is known from the aforecited copending U.S. application Ser. No. 565,008 and from an article titled "Absorption Coefficient Measurement of Nitrous Oxide in Methane at DF Laser Wavelengths" appearing in *Applied Physics Letters*, Vol. 26, No. 6, of Mar. 15, 1975, pages 300–303, to serially arrange a pair of substantially identical optoacoustic detection cells along the laser beam path and to subtract the absorption signals derived from each of the cells to cancel unwanted background. It is also known from this prior article to provide a manually controlled micrometer adjustment mounted to one of the optoacoustic detector cells so as to effect small changes in the volume of one of the cells relative to the other for trimming and equalizing the fluid pressure in the two cells. The absorption lines of various sample constituents are known to have line widths which are pressure sensitive. Therefore it is desired to obtain equalized pressure in the differential cell arrangement, i.e., pressure differentials preferably less than $1 \times 10^{-2}$ torr. However, it is desired that this pressure control be obtained automatically and that provision be made for accurately controlling the pressures for the case of flowing samples in the two cells.

It is also known from the prior art to dispose the optoacoustic cell of an infrared laser absorption spectrometer inside the optical cavity at the laser for increasing the power density of the laser beam within the optoacoustic cell. This substantially improves the sensitivity of the spectrometer for a given laser power and furthermore has several other significant advantages such as producing more laser lines of more nearly equal power. Such an infrared laser absorption spectrometer is disclosed and claimed in copending U.S. application Ser. No. 499,442 filed Aug. 22, 1974, now issued as U.S. Pat. No. 3,893,771 on July 8, 1975.

SUMMARY OF THE PRESENT INVENTION

The principal object of the present invention is the provision of an improved infrared laser absorption spectrometer of the type employing a dual optoacoustic detector.

In one feature of the present invention, a pressure controller is provided which is responsive to the difference in the pressure in the two optoacoustic sample cells, at a frequency substantially below the laser beam modulation frequency, for automatically controlling this pressure differential.

In another feature of the present invention, this automatic pressure controller includes a compliant partitioning means for partitioning one sample cell from the other. The deflection of the partitioning means serves to effect changes in the volume and/or flow rate through the respective cells to maintain a desired pressure control in the two cells.

In another feature of the present invention, a deflectable partitioning means serves to partition the first and second sample cells from each other and acoustic isolation is employed for isolating the deflectable partition from acoustic pressure differences between the two cells at the beam modulation frequency.

In another feature of the present invention, a common deflectable partition partitions the two optoacoustic sample cells and a first component of the deflection of the partition is detected at the beam modulation frequency to derive the infrared absorption difference signal and the second component of the deflection is also detected at frequencies substantially below the beam modulation frequency for controlling the pressure difference in the two cells.

Other features and advantages of the present invention will become apparent upon a perusal of the following specification taken in connection with the accompanying drawings wherein:

BRIEF DESCRIPTION of THE DRAWINGS

FIG. 2 is an enlarged detailed view of an alternative embodiment of that portion of the structure of FIG. 1 delineated by line 2—2, FIG. 3 is an alternative embodiment of that portion of the structure of FIG. 1 delineated by line 3—3.

DESCRIPTION OF THE PREFERRED EMBODIMENT

Figure 1:
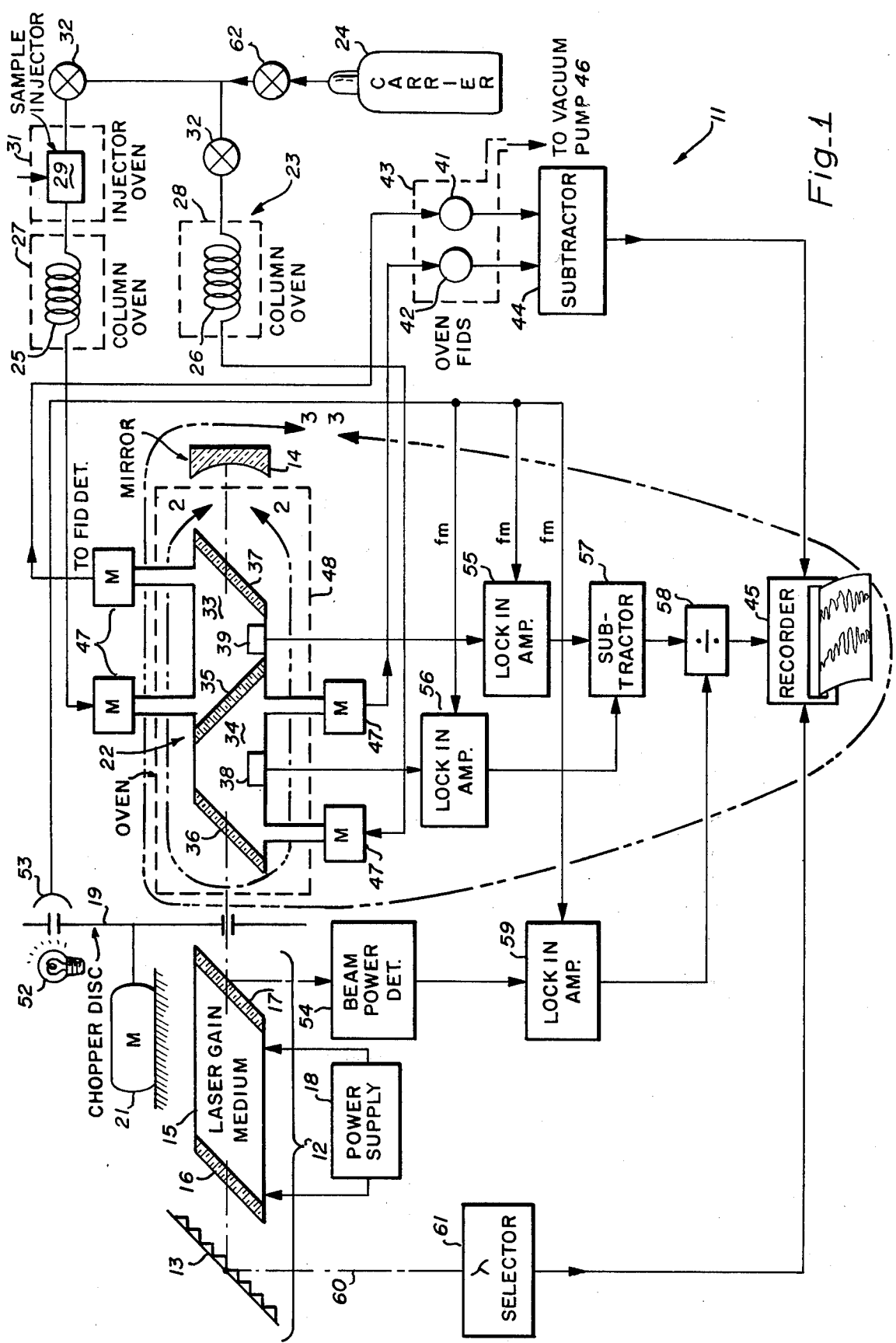
FIG. 1 is a schematic diagram, partly in block diagram form, of a combined infrared laser absorption spectrometer and retention time chromatograph incorporating features of the present invention.

Referring now to FIG. 1, there is shown an infrared laser absorption spectrometer 11 incorporating features of the present invention. Briefly, the spectrometer 11 includes an optical cavity resonator 12 defined by the optical path between a diffraction grating 13 (wavelength selector) and a totally reflective mirror 14. A gas tight envelope 15, having Brewster angle windows 16 and 17 at opposite ends thereof, contains a conventional gaseous gain medium, such as carbon monoxide, carbon dioxide or a helium-neon mixture. The gain medium is interposed along the optical resonator path between the grating 13 and the mirror 14. The gain medium is excited by a suitable electrical discharge to provide coherent stimulated emission radiation at a resonant optical wavelength of the optical resonator 12. Power is supplied from a power source 18 to the gain medium to sustain the electrical discharge and the laser beam within the optical resonator 12 and inbetween opposite ends thereof.

The laser beam is modulated by means of a rotatable perforated chopper disc 19 driven by a motor 21. The speed of rotation of the chopper disc 19 and the spacing between the perforations in the disc 19 control the modulation frequency. In a typical example, the modulation frequency falls within the range of 10 to 400 Hertz.

At dual cell optoacoustic detector 22 is disposed in the beam path for interposing a sample medium, the infrared absorption of which is to be measured by the infrared laser absorption spectrometer 11, in the laser beam.

In the system of FIG. 1, the dual cells of the detector cells 22 are arranged for measuring the absorption of infrared radiation by the effluent of a gas chromatograph 23. The gas chromatograph 23 includes a source 24 of carrier gas, such as helium, which is piped via suitable conduit through a pair of essentially identical retention time chromatographic columns 25 and 26 each contained within its respective column oven 27 and 28 operating at the same temperature. A sample injector 29 is connected into one of the columns 25 upstream thereof for injecting a sample material to be analyzed into the carrier gas stream fed through column 25. The sample injector is contained within its own oven 31. Regulator valves 32 are provided for regulating the flow through each of the respective columns 25 and 26 so that the flow therethrough is essentially identical.

The chromatographic columns 25 and 26 serve to separate the various condensable constituents of the sample material in the fluid stream in accordance with their respective retention times for a specific packing material of the column and for the particular temperature of the column. Effluent streams from the respective columns 25 and 26 are fed to respective cell regions 33 and 34 of the dual cell detector 22. The cell regions 33 and 34 are serially spaced apart along the laser beam path inside the optical resonator 12. The cells are partitioned one from the other via the intermediary of a Brewster angle gas tight window 35. Opposite ends of the dual detector cell 22 are closed off via Brewster angle windows 36 and 37. Individual detector cell regions 33 and 34 are dimensioned to be substantially identical and each contains a respective microphone 39 and 38 coupled in acoustic wave energy exchanging relation with the fluid within the respective cell.

An output port is provided in each of the cell regions 33 and 34 exhausting the sample gas from the cell and for feeding the exhaust gas to a respective flame ionization detector 41 and 42 of conventional design, each being contained within a common oven 43. Output signals from the flame ionization detectors are fed to a subtractor 44 for subtraction to derive a difference signal which is fed to one input of a recorder 45. Flame ionization detectors 41 and 42 are exhausted via an exhaust port to a vacuum pump 46. The vacuum pump is set to pump at such a rate as to preferably cause the flame ionization detectors 41 and 42, as well as the optoacoustic cells 33 and 34, to operate at subatmospheric pressure to prevent undue pressure line broadening of the infrared absorption lines of the sample constituents.

Mufflers 47 are coupled in line with both the input and output gas lines to the respective optoacoustic cells 33 and 34 to prevent coupling of unwanted noise into the optoacoustic cells and to prevent escape of the acoustic wave energy generated therein. The provision of mufflers in cojunction with the optoacoustic cell is disclosed and claimed in copending U.S. application Ser. No. 551,232, filed Feb. 20, 1975, now issued as U.S. Pat. No. 3,897,304 on Oct. 19, 1976.

An oven 48 is disposed around the dual detector cell 22 for maintaining the detector cells 33 and 34 at a desired temperature to prevent undue temperature fluctuations of the dual detector cell in use. A light source 52 directs a beam of light through perforations of the disc 19 to a photodetector 53 as they come into alignment with the source 52 to produce an output corresponding to the modulation frequency of the laser beam. A beam power detector 54 is arranged to pick up a small amount of the beam power which is reflected from one of the Brewster angle windows 17 of the laser tube 15 to produce an output proportional to the beam power.

In operation, absorption of indrared radiation from the laser beam by sample constituents in the detector cells 33 and 34 produces a corresponding heating in each cell region 33 and 34 resulting in generation of an acoustic wave in each cell at the laser beam modulation frequency. These acoustic waves are picked up by respective microphones 39 and 38 and thence fed to respective inputs of lock-in amplifiers 55 and 56 wherein they are amplified against a reference at the beam modulation frequency derived from the photo detector 53. the respective outputs of the lock-in amplifiers 55 and 56 are fed to a subtractor 57 for subtraction therein to derive a difference signal which is then fed to one input of a divider 58. The output of the beam detector 54 is fed to one input of a lock-in amplifier 59 for detection and amplification against the beam modulation frequency reference derived from photo detector 53 to produce an output signal which is fed to the other input of the divider 58 for division into the difference absorption signal for normalization of the difference signal to the beam power.

The normalized difference signal is thence fed to the recorder 45 for recording as a function of retention time and as a function of the wavelength of the infrared laser beam energy. The wavelength is determined by a wavelength selector 61 which, via suitable mechanical linkage 60, changes the angle of the grating 13 to cause the laser to operate on certain predetermined operable wavelengths of the laser. This selected wavelength information is thus fed to the recorder 45 for recording as a function of retention time.

The advantage to the infrared laser optoacoustic spectrometer 11 of FIG. 1 is that contaminants in the carrier gas which are common to both cells produce absorption signals which cancel each other so that essentially only the absorption signal due to the sample material injected by the sample injector 29 appears in the difference output at the output of subtractor 57. Also, unwanted window heating effects similarly cancel. Furthermore, slight fluctuations in temperature and pressure of the system cancel.

As an alternative to using a purified source of carrier gas 24, the carrier gas supply 24 may be disconnected via valve 62 which is a three-way valve so that air may be admitted as the carrier. Although the air may have contaminants the absorption signals due to these contaminants will cancel in the dual cell geometry detector 22. Another advantage to use of the dual cells 33 and 34 in the optical resonator 12 is that, due to the multiple reflections of the wave energy between the end walls of the optical resonator, the beam power is equalized to identical values in both detector cells 33 and 34 regardless of the differences in absorption of infrared wave energy from the beam by the sample in respective ones of the cells 33 and 34. In other words, since the laser beam passes through the cells 33 and 34 in both directions, within the optical resonator, the power is stabilized in the beam so that the beam power within each of the cells 33 and 34 is identical.

As an alternative to flowing the two samples through the two sample cell regions 33 and 34, such samples are simultaneously valved into and out of the cells at suitable intervals of time. Also, the dual detector cell geometry 22 permits a reference material to be disposed in one of the cells and an unknown material to be disposed in the other cell. When the absorptions are the same in both cells 33 and 34 at a number of wavelengths it is highly indicative that the unknown material corresponds to that of the known material in the reference cell portion of the detector 22. Also, since the output signal is a function of the concentration of the absorbing material and the respective cell, a known concentration of the material may be placed in the reference portion of the cell and the same material introduced into the second cell. By comparing the difference signal, the concentration of the material in the nonreference cell may be ascertained by scaling the difference signal derived at the output of divider 58. Furthermore, the dual cell geometry 22 may be used for detecting changes in absorption characteristics of a sample due to variation of an absorption determining parameter of the sample. For example, pressure, temperature, electric field, magnetic field, ionization, etc., can be varied in one cell relative to the other and the difference signal detected.

Referring now to FIG. 2 there is shown an alternative embodiment of the dual detector cell 22' wherein one end of the dual detector cell 22' is closed off by means of the mirror 14 instead of the Brewster angle window 37, thereby eliminating one of the windows and its associated loss in the optical resonator 12.

Referring now to FIG. 3 there is shown an alternative embodiment of that portion of the apparatus of FIG. 1 delineated by line 3—3. More particularly the structure of FIG. 3 depicts a preferred differential microphone structure and automatic pressure regulator for equalizing the pressure in the two cells 33 and 34. More particularly, each of the serially arranged cells 33 and 34 is made as identical as possible each having its respective input and output windows 36 and 35.

A differential microphone 71 is coupled to each of the cells 33 and 34 via identical tubulation 72 so that acoustic wave energy generated within each of the cells 33 and 34 by absorption of energy from the infrared beam is conducted through the tubulations 72 to opposite sides of an electrically conductive compliant microphone diaphragm 73 which is sealed in a gas tight manner across a cylindrical chamber 72 in electrically insulative relation relative to the walls of the chamber 74.

A pair of fixed perforated capacitor plates 75 are likewise sealed across the cylindrical chamber 72 in axially spaced relation from the deflectable diaphragm 72 on opposite sides thereof and preferably equally spaced from the diaphragm in close relation thereto. The perforated capacitive plates 75 are likewise sealed into the chamber 72 in electrically insulative relation with respect thereto and with respect to each other and to the microphone diaphragm 73.

A radio frequency generator 76 has one output thereof coupled to the diaphragm 73 and the other output coupled to respective capacitive plates 75 via load capacitors 77. The perforations in the capacitor plates 74 are dimensioned so as to provide a very low impedance to acoustic wave energy at the beam modulation frequency $f_m$ so that acoustic wave energy is coupled from each of the cells 33 and 34 via the tubulation 72 directly to opposite sides of the capacitive diaphragm 73.

When the acoustic wave pressure is higher in one of the cells relative to the other it will cause a deflection of the microphone diaphragm 73 toward the capacitor plate connected to the cell having the lower acoustic wave pressure, thereby producing an unbalance in the rf voltage at node 78 relative to that at node 79. The rf signals on nodes 78 and 79 are fed into respective lock-in amplifiers 81 and 82 for lock-in amplification first against a reference signal derived from the source 76 to demodulate the carrier and then lock-in amplification and detection against a sample of the laser beam modulation frequency $f_m$ applied to the other input of the respective lock-in amplifiers 81 and 82. The phase of one of the beam modulation frequency components fed into one of the lock-in amplifiers 81 or 82 is variable by phase shifter 83 as required to compensate for slight phase shifts encountered in the acoustic wave energy passing through the conduits 72 to the differential microphone 71.

The outputs of the lock-in amplifiers are fed to a differential amplifier 84 to derive a difference signal corresponding to the difference in the pressure within the chambers 33 and 34. This difference signal is thence fed to a divider 85 for dividing by a signal derived from the beam power lock-in amplifier 59 to derive a normalized difference absorption signal which is fed to the recorder 45 for recording as a function of retention time, wavelength of the infrared radiation, and the difference in the flame ionization detector outputs.

Load capacitors 77 are individually variable to compensate for slight physical displacements of the microphone diaphragm 73 relative to the respective capacitor plates 75. In operation, a pure carrier gas is fed into both cells 33 and 34 and the load capacitors 77 and phase shifter 83 are adjusted to produce a null of the difference signal at the output of differential amplifier 84. The sample material to be analyzed is fed, as by injection, into the carrier stream fed into one of the sample cells relative to the other to produce a difference signal corresponding only to absorption characteristics of the sample under analysis.

As an alternative to adjustment of the phase shifter 83, an adjustable impedance to pressure transmission, such as a bellows 88, is provided in one of the tubulations 72 to equalize the impedance of pressure transmission through both of the tubulations 72 to the differential microphone for the acoustic wave energy. The volume of the acoustic wave passages to the differential microphone 71 is trimmed via adjustable bellows 89 which adjust the volume of one of the tubulations to be equal to that of the other. In this manner the phase shifts for the acoustic wave energy can be adjusted so that they are equal through both of the passages 72 to the differential microphone 71.

An automatic pressure regulator for maintaining the pressure equal in both of the sample chambers 33 and 34 is shown at 91. The pressure regulator includes an enlarged cylindrical chamber 92 coupled in gas communication with each of the cells 33 and 34 via tubulations 93. Acoustic isolators or mufflers 94 are provided in each of the tubulations 93 for acoustically isolating the chamber 92 from the respective cells 33 and 34 at the laser beam modulation frequency $f_m$ without substantially isolating the chamber 92 from the sample chambers 33 and 34 at frequencies substantially below the beam modulation frequency. A thin flexible gas impervious diaphragm 95 is sealed across the chamber 92 in gas tight manner at the periphery thereof for partitioning the chamber 92 into a pair of regions in gas communication with each of the cells 33 and 34. The compliance of pressure diaphragm 95 is made substantially greater than the compliance of the microphone diaphragm 73 so that the pressure diaphragm 95 will move in the required direction as necessary to equalize the pressure in both of the cells 33 and 34 without causing deflection of the microphone diaphragm 73.

Since the infrared absorption lines of most of the sample constituents are pressure sensitive, the automatic pressure regulator 95 serves to reduce unwanted background signals due to pressure differences in each of the respective sample cells 33 and 34. The mufflers 94 serve the purpose of preventing a short circuit of acoustic wave energy from one cell into the other.

Since the diaphragm 95 is operatively only between its extremes of travel, a pair of electrical switches 98 and 99 are provided for sensing each extreme of travel of the diaphragm 95 by closing a circuit to the diaphragm which is made conductive and biased by a voltage source 101. A sensed extreme signal is fed to control a restriction 102 in one of the exhausts of one of the cells 33 to increase the value of the restriction when switch 99 is actuated and to reduce the restriction when switch 98 is actuated.

The advantage of the differential microphone 71 as contrasted with the use of separate microphones in each of the sample chamber cells 33 and 34 is that only one microphone structure is utilized such structure being common to both the cells 33 and 34 to facilitate balancing of the microphone and eliminating the requirement for a second microphone.

Figure 4:
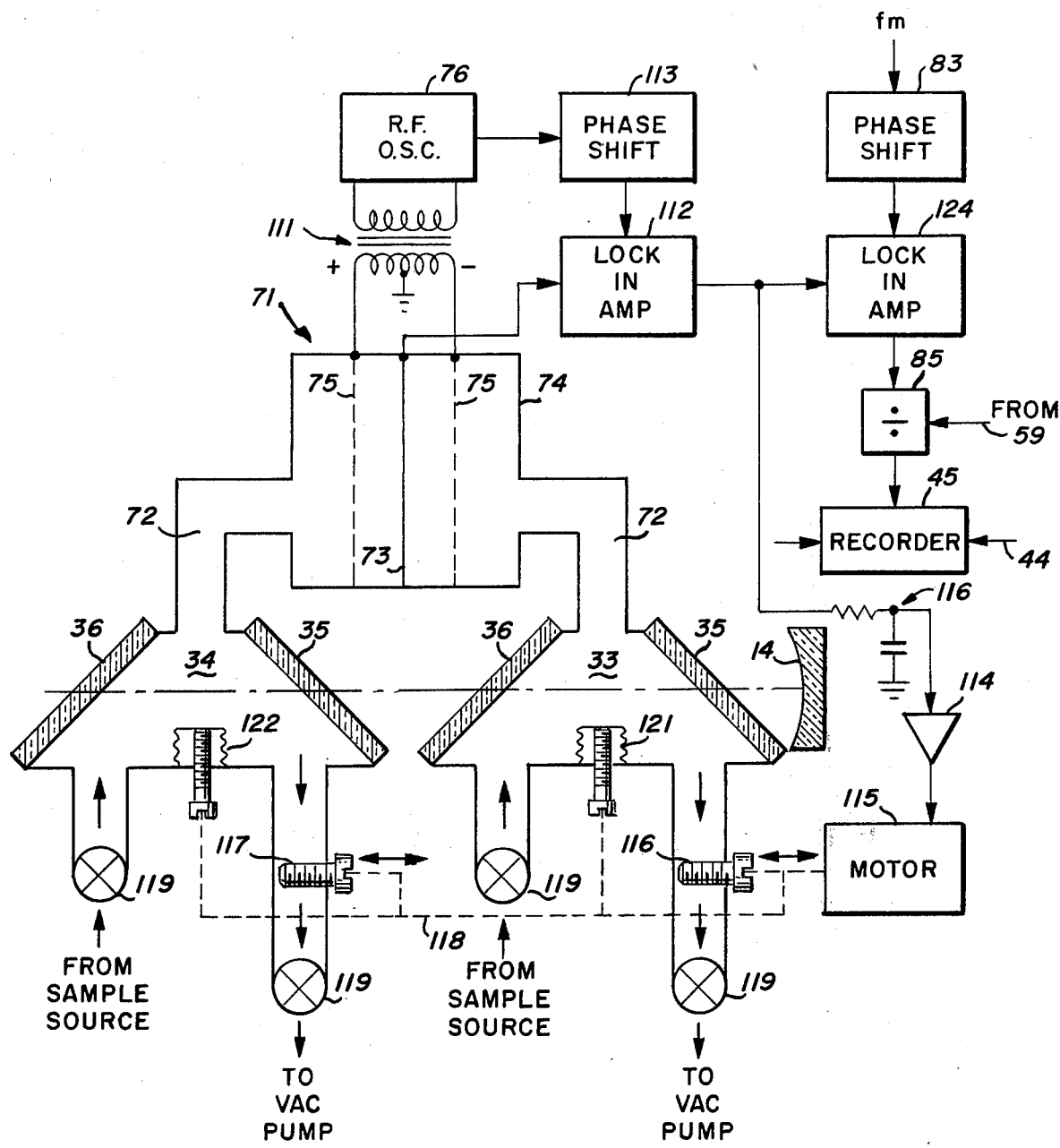
FIG. 4 is an alternative embodiment to the structure of FIG. 3.

Referring now to FIG. 4, there is shown a preferred embodiment of the present invention. The system of FIG. 4 is similar to that of FIG. 3 except that portions of the pressure controller apparatus are common to the structure of the differential microphone 71. The same reference numerals have been employed to designate similar structure. The differential microphone 71 is similar to that of FIG. 3 with the exception that the diaphragm 73 is made more compliant than that of the microphone of FIG. 3 so that the microphone diaphragm 73 will deflect more with a smaller pressure differential to derive an output signal for controlling the pressure in the optoacoustic cells 33 and 34.

The perforated capacitor plates 75 are driven from opposite ends of the secondary of an RF transformer 111, the primary of which is driven from the output of the RF oscillator 76. The center of the secondary of the transformer 111 is grounded. The microphone diaphragm 73 is connected to one input of a lock-in amplifier for lock-in detection (synchronous detection) against a sample of the RF oscillator signal derived from the RF oscillator 76 via a phase shifter 113.

The function of the lock-in amplifier 112 is to demodulate the RF signal derived from the microphone 71. The output of the lock-in amplifier 112 includes a very low frequency component which is substantially below the beam modulation frequency and which corresponds to the pressure difference between the two cells 33 and 34. The output signal from lock-in amplifier 112 includes a second component at the beam modulation frequency, as of a few Hertz to a few hundred Hertz.

The low frequency component in the output of the lock-in amplifier 112 is separated therefrom via a low pass filter 113 and fed through a power amplifier 114 to drive a DC motor 115 which has its output shaft coupled via suitable conventional mechanical linkage to a pair of adjustable restrictions 116 and 117 in the output flow paths of the sample cells 33 and 34, respectively. The drive mechanism 118 and the threads on the adjustable restrictions 116 and 117 such as screws, are reversed or arranged so that the adjustments 116 and 117 operate in opposite senses. More particularly, as the shaft of the motor 115 is turning in certain directions it serves to increase the restriction in one of the output lines and to decrease the restriction in the other output line. In this manner, the back pressure in the cells 33 and 34 is adjusted to reduce the low frequency or DC pressure differentials between the two cells 33 and 34.

As an alternative, the two cells 33 and 34 may be valved off from the source and the vacuum pump via valves 119, in which case the output shaft 118 and screws drive a pair of adjustable bellows 121 and 122, in respective cells 33 and 34, for effecting changes in the ratio of the volumes of the two cells so as to equalize the pressure therebetween and reduce the DC or quasi-DC pressure differential signal to zero. Again, the adjustable bellows 121 and 122 are driven from the output drive 118 in opposite senses so that the volume in one of the cells is increasing when it is decreasing in the other cell.

Phase shifter 113 is provided for adjusting the RF reference as fed into the lock-in amplifier 112 so that slight mechanical mis-alignments of the microphone diaphragm 73 relative to the capacitive plates 75 can be compensated.

The output of the lock-in amplifier 112 is also fed to the input of a second lock-in amplifier 124 for synchronous detection against a signal at the beam modulation frequency $f_m$ as derived from the photodetector 53 via a phase shifter 83. The output of the lock-in amplifier is very low frequency or DC signal having a phase and amplitude corresponding to the acoustic wave pressure differences in the cells 33 and 34. The output of the lock-in amplifier 124 is fed to one input of the divider 85 for division by a sample of the beam power signal derived from lock-in amplifier 59 to derive a difference absorption signal normalized to the beam power. This signal is thence fed to recorder 45 for recording therein as a function of the wavelength of the laser beam energy and/or the difference output signal derived from flame ionization detector 44.

While the deflection of the microphone diaphragm 73 is conveniently detected by means of the applied RF voltage and the capacitive plates 75, other alternative means may be employed for detecting the deflection of the diaphragm 73. Such other alternatives may include magnetic inductive devices, strain gauges mounted to the diaphragm, and the like.

The advantage to the combined differential microphone 71 and pressure controller of FIG. 4 is that the structure is substantially simplified as contrasted with that of FIG. 3, inasmuch as the pressure equalizing diaphragm 95 and associated mufflers 94 are eliminated. Furthermore, both the differential absorption signal, at the beam modulation frequency, and the quasi-static pressure differences between the two cells 33 and 34 are detected by a common differential microphone structure 71.

What is claimed is:

1. In an infrared laser absorption detection apparatus:
    means for producing a laser beam of coherent radiation;
    means for providing first and second sample regions partitioned from each other;
    means for disposing first and second fluid samples in said respective first and second sample regions;
    means for directing at least a portion of the laser beam into at least one of said sample regions for irradiating said sample and for absorbing coherent radiation from the laser beam and for converting the absorbed coherent radiation into a second form of energy, wherein said second form of energy may be a pressure or acoustic wave;
    means for modulating the laser beam at a modulation frequency to produce modulation of the infrared absorption and thus a modulation of the second form of energy;
    absorption detector means coupled in energy exchanging relation with at least said irradiated sample region for detecting the modulated second form of energy resulting from the absorption of energy from the coherent infrared beam by said irradiated sample; and
    pressure controller means responsive to the pressure difference between the sample fluid pressure in said first and second sample regions at a frequency different than the beam modulation frequency for controlling such pressure differential to a predetermined value including zero.

2. The apparatus of claim 1 wherein said pressure controller means includes, means for controlling said pressure differential such as to substantially equalize the fluid pressure in said two sample regions.

3. The apparatus of claim 2 wherein said pressure controller means includes, compliant partitioning means for partitioning the fluid in said first sample region from the fluid in said second sample region, said compliant partitioning means being deflectable in response to a pressure difference in said two sample regions so as to change the ratio of the volumes of fluid in said two partitioned sample regions to automatically reduce the pressure differential therebetween.

4. The apparatus of claim 3 including, acoustic isolation means for rendering said deflectable partitioning means substantially nonresponsive to pressure differences between said first and second sample regions at the laser beam modulation frequency.

5. The apparatus of claim 4 wherein said acoustic isolation means comprises a pair of acoustic muffler means disposed on opposite sides of said partitioning means, respective ones of said muffler means being connected in fluid communication between said partitioning means and respective ones of said sample regions.

6. The apparatus of claim 3 wherein said second form of energy is a pressure wave and said detector means for detecting the modulated second form of energy and said means for deriving an output corresponding to the difference between the detected second form of energy derived from said first and second sample regions includes, a second compliant partitioning means for partitioning the fluid in said first sample region from the fluid in said second sample region, said second compliant partitioning means being deflectable in response to a pressure difference in said two sample regions at the laser beam modulation frequency, and means for detecting the deflection of said second compliant partitioning means to derive an output corresponding to the pressure difference between the fluid pressure in said first and second sample regions, if any, at the beam modulation frequency or harmonics thereof.

7. The apparatus of claim 6 wherein said means for detecting the deflection of said second partitioning means includes, means for producing an electrical reactance which is a function of the deflection of said partitioning means, means for establishing an alternating electrical signal between said second partitioning means and said reactance producing means, and means for deriving a difference output which is a function of the difference in the established electrical signal, at the frequency of the impressed alternating voltage, between said partitioning means and said respective electrical reactance producing means.

8. The apparatus of claim 7 wherein said means for deriving said difference output includes, synchronous detector means for synchronously detecting the alternating signal established between said reactance producing means and said second partitioning means at the frequency of the impressed alternating signal.

9. The apparatus of claim 1 including, fluid conduit means for flowing at least one of the samples through one of said sample regions, and wherein said pressure controller means includes, flow control means for controlling flow of the sample through said fluid conduit means in response to the pressure difference between said first and second sample regions so as to control the pressure differential between said first and said second sample regions.

10. The apparatus of claim 9 wherein said pressure controller means includes, compliant partitioning means for partitioning the fluid in said first sample region from the fluid in said second sample region, said compliant partitioning means being deflectable in response to a pressure difference in said two sample regions, and means responsive to the deflection of said compliant partitioning means for automatically controlling the pressure differential between the fluid in said first and second sample regions.

11. The apparatus of claim 10 including, means responsive to a predetermined deflection of said compliant partitioning means in a certain direction to derive a limit output, and wherein said flow control means is responsive to said limit output to change the rate of sample flow through said conduit means so as to cause said partitioning means to move in the opposite direction to said certain direction.

12. The apparatus of claim 1 wherein said pressure controller means includes, deflectable partitioning means for partitioning the fluid in said first sample region from the fluid in said second sample region, said deflectable partitioning means being deflectable in response to a pressure difference in said two sample regions, deflection detecting means for detecting a deflection of said partitioning means in response to a pressure difference between the fluid pressure in said first and second sample regions to derive a difference output, and pressure correcting means responsive to said difference output for controlling said pressure difference between said first and second sample regions.

13. The apparatus of claim 12 wherein said pressure correcting means includes, means responsive to said difference output volumes changing the ratio of the volume of said first and second sample regions so as to control the pressure differential therebetween.

14. The apparatus of claim 12 including, fluid conduit means for flowing at least one of the fluid samples through one of said sample regions, and wherein said pressure correcting means includes, flow control means for controlling the flow of the fluid sample through said fluid conduit means so as to control the fluid pressure differential between said first and second sample regions.

15. The apparatus of claim 12 wherein said absorption detecting means comprises, means for detecting a deflection component of said partitioning means at the beam modulation frequency or harmonics thereof, and wherein said difference detecting means comprises means for detecting a deflection component of said partitioning means at a frequency different than the beam modulation frequency.

16. The apparatus of claim 15 wherein said partitioning means is common to both of said absorption detecting means and said difference detector means.

17. The apparatus of claim 1 wherein said pressure controller means has a maximum frequency response substantially lower in frequency than that of said beam modulation frequency, whereby said absorption detector means, at said beam modulation frequency, is not substantially adversely affected by operation of said pressure controller means.

18. The apparatus of claim 2 wherein the second form of energy is acoustic wave energy and wherein said absorption detecting means includes a differential microphone means for sensing acoustic wave pressure differences, at the beam modulation frequency or harmonics thereof, between the first and second sample regions and having a first side thereof coupled in acoustic wave energy exchanging relation, at the beam modulation frequency or harmonics thereof, with said first sample region and having a second side thereof coupled in acoustic wave energy exchanging relation, at said beam modulation frequency or harmonics thereof, with said second sample region.

19. The apparatus of claim 18 wherein said pressure controller means has a maximum frequency response substantially lower in frequency than that of said beam modulation frequency, whereby said absorption detector means, at said beam modulation frequency or harmonics thereof, is not substantially adversely affected by operation of said pressure controller means.

* * * * *